(12) United States Patent
Hölzl et al.

(10) Patent No.: US 6,689,372 B1
(45) Date of Patent: Feb. 10, 2004

(54) MICROBICIDAL ACTIVE SUBSTANCES

(75) Inventors: Werner Hölzl, Eschentzwiller (FR); Marcel Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/762,008

(22) PCT Filed: Jul. 30, 1999

(86) PCT No.: PCT/EP99/05449

§ 371 (c)(1),
(2), (4) Date: Feb. 1, 2001

(87) PCT Pub. No.: WO00/07446

PCT Pub. Date: Feb. 17, 2000

(65) Prior Publication Data (65)

(30) Foreign Application Priority Data

Aug. 4, 1998 (EP) ............................................ 98810749

(51) Int. Cl.⁷ ........................ A01N 25/00; A01N 43/82; A61K 6/00; A61K 7/00; A61K 31/41
(52) U.S. Cl. ...................... 424/405; 424/401; 514/360; 514/439; 514/448
(58) Field of Search ................................ 424/401, 404, 424/405; 514/360, 439, 448, 463

(56) References Cited

U.S. PATENT DOCUMENTS

| | | | | |
|---|---|---|---|---|
| 4,144,047 A | * | 3/1979 | Franz et al. | 71/90 |
| 4,187,099 A | * | 2/1980 | Franz et al. | 71/90 |
| 4,261,728 A | * | 4/1981 | Franz et al. | 71/88 |
| 4,724,246 A | * | 2/1988 | Ravichandran | 524/83 |
| 5,028,412 A | * | 7/1991 | Putt et al. | 424/48 |
| 5,114,958 A | * | 5/1992 | Boschelli et al. | 514/361 |
| 5,294,438 A | * | 3/1994 | Chang et al. | 424/73 |
| 5,356,803 A | * | 10/1994 | Carpenter et al. | 435/200 |
| 5,446,059 A | * | 8/1995 | Rocher et al. | 514/374 |
| 5,672,351 A | * | 9/1997 | Chikindas et al. | 424/401 |
| 5,736,545 A | * | 4/1998 | Gadwood et al. | 514/252 |
| 5,977,373 A | * | 11/1999 | Gadwood et al. | 548/128 |
| 5,998,487 A | * | 12/1999 | Brahms et al. | 514/736 |
| 6,007,795 A | * | 12/1999 | Masterman et al. | 424/49 |

FOREIGN PATENT DOCUMENTS

| | | |
|---|---|---|
| GB | 1079348 | 8/1967 |
| WO | 96/17835 | 6/1996 |

OTHER PUBLICATIONS

Senning et al., Acta. Chem. Scand., vol. 27, No. 6, (1973), pp. 2161–2170.

* cited by examiner

Primary Examiner—Sreeni Padmanabhan
Assistant Examiner—Lauren Q. Wells
(74) Attorney, Agent, or Firm—Kevin T. Mansfield

(57) ABSTRACT

The use of oxathiazolones of formula

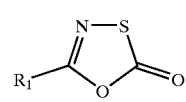

(1)

is described $R_1$ is phenyl unsubstituted or substituted by one or more $C_1$–$C_5$ alkyl, hydroxyl, halogen substituents or by a 1,3,4-oxathiazol-2-one radical.

in the antimicrobial treatment of surfaces.

The compounds exhibit a pronounced action against pathogenic gram-positive and gram-negative bacteria, and also against yeasts and moulds.

3 Claims, No Drawings

MICROBICIDAL ACTIVE SUBSTANCES

This is a 371 of PCT/EP99/05449, filed Jul. 30, 1999, which claims priority to EP 98810749.6 filed Aug. 4, 1998.

The present invention relates to the use of oxathiazolones in the antimicrobial treatment of surfaces.

The oxathiazolones used according to the invention correspond to formula

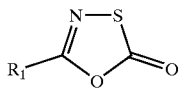

(1)

wherein $R_1$, is $C_1$–$C_{16}$alkyl, $C_2$–$C_{16}$alkenyl or $C_5$–$C_8$cycloalkyl, each unsubstituted or substituted by halogen, —CN, —$NO_2$, —C=O, —C=S, —$NR_2$, —$OR_3$, —$SR_4$, —$SO_2R_5$, —$COOR_6$ or by a 1,3,4-oxathiazol-2-one radical; $C_6$–$C_{10}$aryl unsubstituted or substituted by one or more $C_1$–$C_5$alkyl, $C_6$–$C_{10}$aryl, halogen, hydroxy, acyl, —CN, —$CF_3$, —$NO_2$, —$NR_2$, —$OR_3$, —$SR_4$, —$SO_3H$, —$SO_2R_5$, —$COOR_6$ substituents or by a 1,3,4-oxathiazol-2-one radical; or a 5- or 6-membered heterocyclic radical;

$R_2$ and $R_3$ are each independently of the other hydrogen; $C_1$–$C_5$alkyl; $C_6$–$C_{10}$aryl, or acyl;

$R_4$ is hydrogen; $C_1$–$C_5$alkyl; or $C_6$–$C_{10}$aryl;

$R_5$ is $C_1$–$C_5$alkyl; or $C_6$–$C_{10}$aryl;

$R_6$ is hydrogen; $C_1$–$C_5$alkyl; or $C_6$–$C_{10}$aryl.

$C_1$–$C_{16}$Alkyl are straight-chain or branched alkyl radicals, e.g. methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl or hexadecyl.

$C_2$–$C_{16}$Alkenyl is e.g. allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, 3,6,8-decatrienyl or isododecenyl.

$C_6$–$C_{10}$Aryl can be a mono- or bi-cyclic aromatic radical, e.g. phenyl or naphthyl.

$C_5$–$C_8$Cycloalkyl can be cyclopentyl, cycloheptyl, cyclooctyl or preferably cyclohexyl.

Examples of 6-membered heterocyclic radicals are pyranyl, pyridyl, pyrazinyl, pyrimidinyl, pyridazinyl, piperazinyl, indolinyl and morpholinyl.

Examples of 5-membered heterocyclic radicals are thienyl, furyl, 2H-pyrrolyl, pyrrolyl, imidazolyl, pyrazolyl, isoxazolyl, furazanyl, pyrrolidinyl, pyrrolinyl, imidazolidinyl, pyrazolidinyl and pyrazolinyl.

The 5- or 6-membered heterocyclic radicals can be unsubstituted or substituted by halogen, such as chlorine or bromine, nitro, $C_1$–$C_5$alkyl or by $C_1$–$C_5$alkoxy.

According to the invention, preference is given to the use of compounds of formula (1) wherein $R_1$ is $C_1$–$C_{16}$alkyl unsubstituted or substituted by halogen, —CN, —$NO_2$, —C=O, —C=S, —$NR_2$, —$OR_3$, —$SR_4$, —$SO_2R_5$, —$COOR_6$ or by a 1,3,4-oxathiazol-2-one radical; or $C_6$–$C_{10}$aryl unsubstituted or substituted by one or more $C_1$–$C_5$alkyl, $C_6$–$C_{10}$aryl, halogen, hydroxy, acyl, —CN, —$CF_3$, —$NO_2$, —$NR_2$, —$OR_3$, —$SR_4$, —$SO_3H$, —$SO_2R_5$, —$COOR_6$ substituents or by a 1,3,4-oxathiazol-2-one radical; and $R_2$, $R_3$, $R_4$, $R_5$ and $R_6$ are as defined for formula (1).

Special preference is given to compounds of formula (1) wherein $R_1$ is $C_1$–$C_{16}$alkyl; especially $C_1$–$C_{12}$alkyl and more especially methyl or ethyl.

According to the invention, use is also preferably made of oxathiazolones of formula

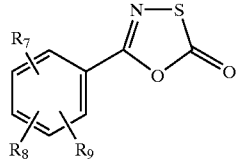

(2)

wherein $R_7$, $R_8$ and $R_9$ are each independently of the others hydrogen; halogen; hydroxy; or $C_1$–$C_5$alkyl.

Examples of compounds that can be used according to the invention correspond to formulae

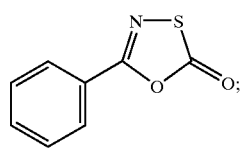

(3)

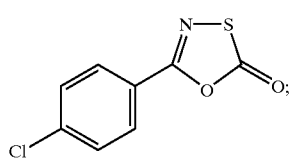

(4)

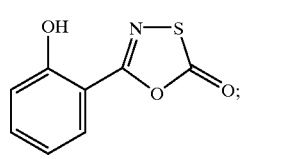

(5)

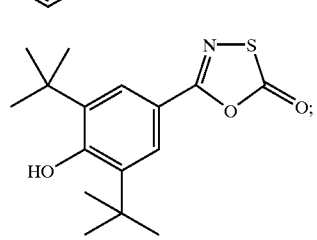

(6)

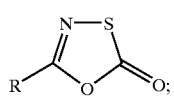

(7)

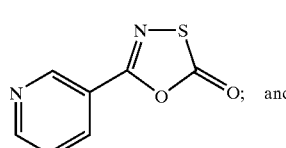

(8)

and

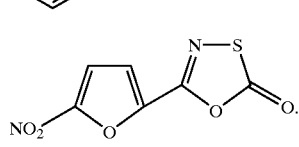

(9)

In formula (7), R=—$CH_3$; or —$(CH_2)_{10}CH_3$.

The compounds of formulae (1) to (8) are known in the literature. The compound of formula (9) is a new compound.

The preparation of the oxanilides used according to the invention is effected in accordance with known procedures by reacting a carboxylic acid amide of formula

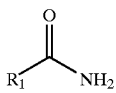
(10)

with chlorocarbonylsulfenic acid chloride, corresponding to formula

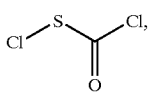
(11)

in accordance with the following scheme:

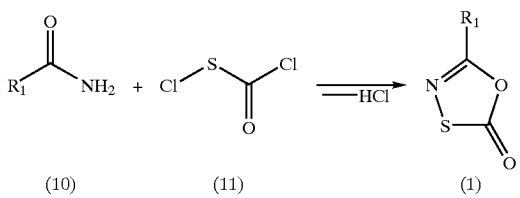

(10)    (11)    (1)

wherein $R_1$ is as defined for formula (1).

The starting materials corresponding to formula (7) are known. Chlorocarbonylsulfenic acid chloride (compound of formula (11)) is a known reagent of organic chemistry.

The preparation process is preferably carried out without an acid acceptor but can also be carried out in the presence of a suitable acid acceptor. As such there come into consideration all customary organic and inorganic bases. These include, for example, alkaline earth metal and alkali metal hydrides, hydroxides, amides, alcoholates, acetates, carbonates and hydrogen carbonates, e.g. sodium hydride, sodium amide, sodium methanolate, sodium ethanolate, potassium tert-butanolate, sodium hydroxide, potassium hydroxide, ammonium hydroxide, sodium acetate, potassium acetate, calcium acetate, ammonium acetate, sodium carbonate, potassium carbonate, sodium potassium carbonate or hydrogen carbonate, ammonium carbonate, and also tertiary amines, such as trimethylamine, triethylamine, tributylamine, N,N-dimethylaniline, N,N-dimethylbenzylamine, pyridine, N-methylpiperidine and N,N-dimethylaminopyridine.

The process is preferably carried out in the presence of a solvent. All customary organic solvents come into consideration for that purpose. These include especially aliphatic, alicyclic or aromatic, optionally halogenated hydrocarbons, e.g. benzene, toluene, xylene, chlorobenzene, dichlorobenzene, petroleum ether, hexane, cyclohexane, dichloromethane, chloroform, carbon tetrachloride, ethers, such as dimethyl ether, diethyl ether, dioxane, tetrahydrofuran and ethylene glycol dimethyl ether, ketones, such as acetone, butanone and methyl isobutyl ketone, nitriles, such as acetonitrile, propionitrile and benzonitrile; amides, such as N,N-dimethylformamide, N,N-dimethylacetamide, N,N-methylformanilide, N-methyl-pyrrolidone and hexamethylphosphoric acid triamide; esters, such as methyl acetate and ethyl acetate, sulfoxides, such as dimethyl sulfoxide, preferably hydrocarbons. Special preference is given to toluene and dioxane.

The reaction temperatures can be varied within a wide range. The operation is generally carried out at temperatures of from −10 to +180° C., preferably at temperatures of from 20 to 130° C.

The process is usually carried out under normal pressure, but may also be carried out at elevated or reduced pressure.

For carrying out the process, generally from 1 to 10 mol, preferably from 1.0 to 3 mol, of chlorocarbonylsulfenic acid chloride are used per mole of carboxylic acid amide of formula (10).

The oxathiazolones used according to the invention exhibit a pronounced antimicrobial action, especially against pathogenic gram-positive and gram-negative bacteria and also against bacteria of skin flora, e.g. *Corynebacterium xerosis* (bacteria that cause body odour), and also against yeasts and moulds. They are therefore especially suitable in the disinfection of the skin and mucosa and also of integumentary appendages (hair), more especially in the disinfection of the hands and of wounds.

They are therefore suitable as antimicrobial active ingredients in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention therefore relates also to a personal care preparation comprising at least one compound of formula (1) as well as cosmetically tolerable carriers or adjuvants.

The personal care preparation according to the invention comprises from 0.01 to 15% by weight, preferably from 0.5 to 10% by weight, based on the total weight of the composition, of the oxathiazolone compound of formula (1), and cosmetically tolerable adjuvants.

Depending upon the form of the personal care preparation, it will comprise, in addition to the oxathiazolone compound of formula (1), further constituents, for example sequestering agents, colourings, perfume oils, thickening or solidifying (consistency regulator) agents, emollients, UV absorbers, skin-protective agents, antioxidants, additives that improve mechanical properties, such as dicarboxylic acids and/or Al, Zn, Ca and Mg salts of $C_{14}$–$C_{22}$ fatty acids, and optionally preservatives.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention may be contained in a wide variety of cosmetic preparations. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and anti-perspirants or callous-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or after-shave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations; e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:

0.01 to 5% by weight of the compound of formula (1)
0.3 to 1% by weight titanium dioxide
1 to 10% by weight stearic acid
ad 100% soap base, e.g. the sodium salts of tallow fatty acid and coconut fatty acid or glycerol.

A shampoo has, for example, the following composition:

0.01 to 5% by weight of the compound of formula (1)
12.0% by weight sodium laureth-2-sulfate
4.0% by weight cocamidopropyl betaine
3.0% by weight NaCl and
water ad 100%.

A deodorant has, for example, the following composition:

0.01 to 5% by weight of the compound of formula (1)
60% by weight ethanol
0.3% by weight perfume oil and
water ad 100%.

The invention relates also to an oral composition, comprising from 0.01 to 15% by weight, based on the total weight of the composition, of the compound of formula (1), and orally tolerable adjuvants.

Example of an oral composition:

10% by weight sorbitol
10% by weight glycerol
15% by weight ethanol
15% by weight propylene glycol
0.5% by weight sodium lauryl sulfate
0.25% by weight sodium methylcocyl taurate
0.25% by weight polyoxypropylene/polyoxyethylene block copolymer
0.10% by weight peppermint flavouring
0.1 to 0.5% by weight of a compound of formula (1) and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The oxathiazolones of formula (1) used according to the invention are also suitable for the treatment of textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The oxathiazolones of formula (1) are also used in washing and cleaning formulations, e.g. in liquid or powder washing agents or softeners.

The oxathiazolones used according to the invention are also suitable for imparting anti-microbial properties to plastics, e.g. polyethylene, polypropylene, polyurethane, polyester, polyamide, polycarbonate, latex etc. Fields of use therefor are, for example, floor coverings, plastics coatings, plastics container and packaging materials, kitchen and bathroom utensils (e.g. brushes, shower curtains, sponges, bathmats), latex filter materials (air and water filters), plastics articles used in the field of medicine, e.g. dressing materials, syringes, catheters etc., so-called "medical devices", gloves and mattresses.

Paper, for example papers used for hygiene purposes, may also be provided with anti-microbial properties using the oxathiazolones according to the invention.

It is also possible for nonwovens, e.g. nappies/diapers, sanitary towels, panty liners, and cloths for hygiene and household uses, to be provided with antimicrobial properties in accordance with the invention.

The oxathiazolones can be used especially also in household and all-purpose cleaners for cleaning and disinfecting hard surfaces.

A cleaning preparation has, for example, the following composition:

0.01 to 5% of the compound of formula (1)
3.0% octyl alcohol 4EO
1.3% fatty alcohol $C_8$–$C_{10}$polyglucoside
3.0% isopropanol
ad 100% water.

In addition to preserving cosmetic and household products, technical products, such as paper treatment liquors, printing thickeners of starch or of cellulose derivatives, surface-coatings and paints, can be preserved and provided with antimicrobial properties.

The oxathiazolones of formula (1) are also suitable for the antimicrobial treatment of wood and for the antimicrobial treatment of leather and the provision of leather with antimicrobial properties.

The compounds according to the invention are also suitable for the protection of cosmetic products and household products from microbial damage.

The following Examples serve to illustrate the invention but do not limit the invention to the Examples.

EXAMPLE 1

Preparation of the compound of formula (101)

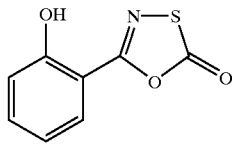

6.5 g (0.05 mol) of chlorocarbonylsulfenyl chloride, dissolved in 60 ml of dioxane, are added to 4.0 g (0.029 mol) of salicylamide. The reaction mixture is heated at reflux for 3 hours. A clear solution is formed. Since TLC (=thin layer chromatography) indicates a small amount of unreacted starting material, a further 0.5 ml of chlorocarbonylsulfenyl chloride is added and heating is continued at reflux, with stirring, for a further one hour.

The solvent is then removed in vacuo and the residue is purified by column chromatography (5% ethyl acetate in petroleum ether).

Yield: 3.8 g (68% of theory)

EXAMPLE 2

Preparation of the compound of formula (102)

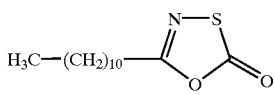

5.0 g (0.025 mol) of lauroyl amide are dissolved in 30 ml of dioxane by heating at 110° C. 5.0 g (0.038 mol) of chlorocarbonylsulfenyl chloride are added to the resulting solution and heating is continued for a further 5 to 6 hours. The reaction is monitored by TLC. When the reaction is complete, the reaction mixture, which still contains some suspended particles, is filtered. The filtrate is concentrated to form a solid compound which is purified by column chromatography (petroleum ether/ethyl acetate mixture).

Yield: 3.87 g (60% of theory)

EXAMPLE 3

Preparation of the compound of formula (103)

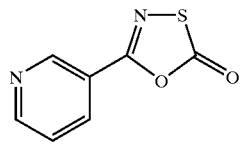

4.5 g (0.036 mol) of nicotine amide are heated at reflux in 20 ml of toluene. 6.5 g (0.05 mol) of chlorocarbonylsulfenyl chloride dissolved in 15 ml of toluene are added to the resulting hot solution. Heating is continued at reflux for a further 6 hours. When the reaction is complete, the reaction mixture is washed with $NaHCO_3$. The solid portion is separated off and purified by column chromatography (petroleum ether/ethyl acetate mixture).

Yield: 1.5 g (23% of theory)

EXAMPLE 4

Prepatation of the compound of formula (104)

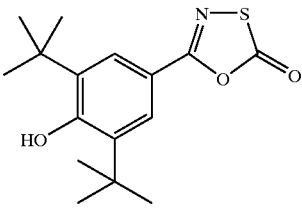

4.35 g (0.033 mol) of chlorocarbonylsulfenyl chloride dissolved in 10 ml of dioxane are added dropwise at reflux temperature to 5.0 g (0.02 mol) of 3,5-di-tert-butyl-4-hydroxybenzamide in 30 ml of dioxane. The reaction starts immediately. The solvent is removed under reduced pressure and the residue is purified by recrystallisation from a petroleum ether/ethyl acetate mixture.

Yield: 2.95 g (48% of theory)

EXAMPLE 5

Preparation of the compound of formula (105)

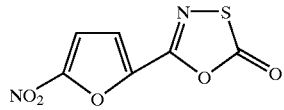

6.0 g (0.038 mol) of 5-nitro-5-furanic acid amide are dissolved in 30 ml of dioxane by heating at 80° C. 7.55 g (0.057 mol) of chlorocarbonylsulfenic acid chloride dissolved in 10 ml of toluene are added to the resulting hot solution and heating is carried out at reflux for 3 hours. When the reaction is complete, the reaction mixture is concentrated under reduced pressure and the residue is purified by recrystallisation from a petroleum ether/ethyl acetate mixture.

Yield: 2.6 g (31.6% of theory)

EXAMPLE 6

Preparation of the compound of formula (106)

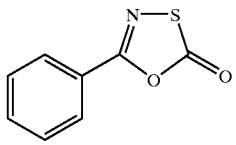

A mixture of 60.5 g (0.5 mol) of benzamide, 65.5 g (0.5 mol) of chlorocarbonylsulfenyl chloride and 250 ml of toluene are cautiously heated, with stirring, at from 60 to 90° C. Towards the end of the HCl evolution after about 2 hours, the reaction mixture is heated for one hour at from 100 to 110° C. After removal of the solvent, the solid residue is recrystallised from petroleum ether/ethyl acetate.

Yield: 44.9 g (50%)

EXAMPLE 7

Preparation of a liquid washing agent

| | |
|---|---|
| 0.01–5% | of the compound of formula (106) |
| 15.0% | PEG-7 $C_{14}$–$C_{15}$ alcohol ether |
| 10.0% | sodium dodecylbenzenesulfonate |
| 10.0% | propylene glycol |
| 3.0% | sodium citrate |
| ad 100% | deionised water |

The compound of formula (106) is dissolved in the $C_{14}$–$C_{15}$ alcohol ether at 50° C. Propylene glycol and sodium dodecylbenzenesulfonate are added and the mixture is stirred until homogeneous. After cooling to 22° C., sodium citrate and water are added.

EXAMPLE 8

Preparation of a softener

| | |
|---|---|
| 0–5% | of the compound of formula (106) |
| 4.0% | of the compound of formula $\begin{bmatrix} & CH_3 & \\ & | & \\ R- & N^+ -R \\ & | & \\ & CH_3 & \end{bmatrix}$ Cl⁻ |
| | R = aliphatic radical of tallow fatty acid |
| 0.5% | pareth-25-7 and |
| ad 100% | deionised water |

The compound of formula (106) is dissolved in Quaternium 18 at 40° C.; pareth-25-7 and water are added and the mixture is stirred until a homogeneous mixture is formed,

EXAMPLE 9

Preparation of a dishwashing agent

| | |
|---|---|
| 0.01–5% | of the compound of formula (106) |
| 7.0% | sodium lauryl sulfate |
| 7.0% | sodium myreth sulfate |
| 4.0% | lauryl glucoside |
| 1.1% | cocobetaine |
| 5.0% | ethanol |
| 1.0% | citric acid |
| ad 100% | deionised water |

The compound of formula (106) is dissolved in ethanol. The surfactants (sodium lauryl sulfate, sodium myreth sulfate, lauryl glucoside and cocobetaine) are added predissolved in water and the mixture is stirred at 40° C. until homogeneous. Citric acid and water are added to the solution at 22° C.

EXAMPLE 10

Preparation of a liquid soap

| | |
|---|---|
| 0.01–5% | of the compound of formula (106) |
| 10.0% | sodium laureth-2-sulfate |
| 3.0% | cocamidopropyl betaine |
| 2.0% | lauryl glucoside |
| 1.0% | glycol distearate |
| 1.0% | sodium chloride |
| ad 100% | deionised water |

The compound of formula (106) is solubilised at 50° C., with stirring, in cocamidopropyl betaine and lauryl glucoside. Sodium laureth-2-sulfate and glycol distearate are added and the mixture is stirred at 50° C. until homogeneous. When the glycol distearate has fully dissolved, the mixture is cooled to room temperature, with stirring; water is added and the viscosity is adjusted with sodium chloride.

EXAMPLE 11

Preparation of a surface disinfectant 0.01 to 5% of the compound of formula (106)
3.0% octyl alcohol 4EO
1.3% fatty alcohol $C_8$–$C_{10}$ polyglucoside
3.0% isopropanol
ad 100% water The compound of formula (106) is dissolved in isopropanol; octyl alcohol 4EO and fatty alcohol $C_8$–$C_{10}$ polyglucoside are added to the solution and the mixture is stirred until homogeneous. The pH value is adjusted with ethanolamine and the formulation is made up to 100% with water.

EXAMPLE 12

Determination of antimicrobial activity in the agar diffusion test

| | |
|---|---|
| Medium: | casein/soybean flour peptone agar (Merck) |
| | * Sabouraud 4% glucose agar (Merck) |
| Dilution medium: | sterile 0.85% NaCl solution |
| Test organisms: | Staphylococcus aureus ATCC 9144 |
| | Escherichia coli NCTC 8196 |
| | Candida albicans ATCC 10231 |
| | * Aspergillus niger ATCC 6275 |
| Incubation of the precultures: | 24 hours at 37° C. |
| | * 5–7 days at 28° C. |
| Incubation of the test plates: | 24 hours at 37° C. |
| | * 4 days at 28° C. |

After the bacteria precultures have been incubated, they are diluted 1:100 with dilution medium.

3.5 ml of that dilution of the bacteria are introduced into 500 ml of agar and from that organism-containing agar plates of about 15 ml of medium are poured.

The test substances are dissolved in a suitable solvent in final concentrations of 1–3%.

After the agar plates have cooled and solidified, wells are punched in the agar (diameter 10 mm) and 100 μl of test substance solution are introduced into each well.

After incubation of the plates, the diameters of the growth-free inhibiting areolas in the agar are determined.

The test results for the compound of formula (107)

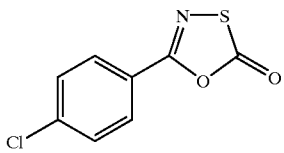

are given in Table 1:

TABLE 1

| | Inhibiting areola diameter (mm) | |
|---|---|---|
| Microorganisms | 2% in ethanol | 1% in ethanol |
| Staphylococcus aureus ATCC 9144 | 5/5 | 4/4 |
| Escherichia coli NCTC 8196 | 1/1 | 1/1 |
| Candida albicans ATCC 10231 | 4/4 | 3/3 |
| Aspergillus niger ATCC 6275 | 0/0 | 0/0 |

The test results for the compound of formula (108)

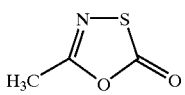

are given in Table 2.

TABLE 2

| | Inhibiting areola diameter (mm) | |
|---|---|---|
| Microorganisms | 2% in ethanol | 1% in ethanol |
| Staphylococcus aureus ATCC 9144 | 20/20 | 12/12 |
| Escherichia coli NCTC 8196 | 3/2 | 1/1 |
| Candida albicans ATCC 10231 | 10/10 | 8/8 |
| Aspergillus niger ATCC 6275 | 12/12 | 4/5 |

The test results for the compound of formula (105) are given in Table 3:

TABLE 3

| | Inhibiting areola diameter (mm) | | | |
|---|---|---|---|---|
| Microorganisms | Staphylococcus aureus ATCC 9144 | Escherichia coli NCTC 8196 | Pseudomonas aeruginosa ATCC 15 442 | Candida albicans ATCC 10 231 |
| Compound of formula (105): | | | | |
| 3.0% in THF | 11/11 | 6/6 | 6/6 | 9/9 |
| 1.0% in THF | 11/11 | 6/6 | 5/5 | 8/8 |
| 0.5% in THF | 10/10 | 3/3 | 1/1 | 4/4 |
| 0.1% in THF | 4/4 | 1/1 | 0/0 | 3/3 |

Determination of the Minimum Inhibiting Concentration (MIC) in the Agar Incorporation Test (MIC Test)

| | |
|---|---|
| Medium: | casein/soybean flour peptone agar (Merck) |
| | * Sabouraud 4% glucose agar (Merck) |
| Dilution medium: | sterile 0.85% NaCl solution |
| Test organisms: | Staphylococcus aureus ATCC 9144 |
| | Staphylococcus epidermidis ATCC 12228 |
| | Corynebacterium xerosis ATCC 373 |
| | Escherichia coli NCTC 8196 |
| | Pseudomonas aeruginosa CIP A-22 |
| | Candida albicans ATCC 10231 |
| | * Aspergillus niger ATCC 6275 |
| Incubation: | 24 hours at 37° C. |
| | * 3 days at 28° C. |
| Test solution: | 1% stock solutions of all the test substances in a suitable solvent are prepared and diluted in dilution series to final concentrations of from 1000 ppm to 10 ppm. |
| Test principle: | 0.3 ml of the dilution stage in question is mixed with 15 ml of still-liquid nutrient medium. |

When the nutrient substrate has solidified, 10 μl portions of the following organism dilutions of the test strains in 0.85% NaCl solution are spotted onto the agar medium:

| | |
|---|---|
| Staphylococcus aureus ATCC 9144 | 1:100 dilution |
| Staphylococcus epidermidis ATCC 12228 | 1:100 dilution |
| Corynebacterium xerosis ATCC 373 | 1:100 dilution |
| Escherichia coli NCTC 8196 | 1:1000 dilution |
| Pseudomonas aeruginosa CIP A-22 | 1:1000 dilution |
| Candida albicans ATCC 10'231 | 1:10 dilution |
| Aspergillus niger ATCC 6275 | 1:10 dilution |

The plates are incubated at 37° C. for 24 hours (A.niger 3 days at 28° C.) and then the highest dilution of the test substance at which growth is just no longer discernible (corresponds to MIC) is determined.

The test results are given in Table 4.

TABLE 4

| Organisms | Compound of formula (106) (solution in DMSO) | Compound of formula (103) (solution in EtOH) | Compound of formula (101) (solution in EtOH) |
|---|---|---|---|
| S. aureus | 10 | 100 | 100 |
| S. epidermidis | 10 | 100 | 100 |
| C. xerosis | 10 | 200 | 250 |
| E. coli | 100 | 600 | 1000 |
| P. aeruginosa | 1000 | 600 | 1000 |
| C. albicans | 100 | 100 | 100 |
| A. niger | 250 | 600 | 100 |

MIC concentrations in ppm

The results show that the test substances exhibit strong antimicrobial activity against gram-postive and gram-negative bacteria and also fungi and yeasts.

What is claimed is:

1. A method of antimicrobial treatment of skin, mucosa or hair which comprises, contacting the surface of the skin, mucosa or hair of a person in need of said antimicrobial treatment with an antimicrobially effective amount of a compound of formula

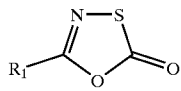

(1)

wherein $R_1$ is phenyl unsubstituted or substituted by one or more C1–C5 alkyl, hydroxyl, halogen substituents or by a 1,3,4-oxathiazol-2-one radical.

2. A method according to claim 1, in which a washing and/or cleaning formulation comprising a compound of formula (1) is used.

3. A method according to claim 1, wherein there is used an oxathiazolone of formula

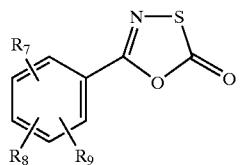

(2)

wherein $R_7$, $R_8$ and $R_9$ are each independently of the others hydrogen; halogen; hydroxy; or $C_1$–$C_5$ alkyl.

* * * * *